(12) United States Patent
Courty et al.

(10) Patent No.: US 7,534,436 B2
(45) Date of Patent: May 19, 2009

(54) PEPTIDE FRAGMENTS OF THE HARP FACTOR INHIBITING ANGIOGENESIS

(75) Inventors: José Courty, Villecresnes (FR); Denis Barritault, Paris (FR); Isabelle Pierrot, Nogent sur Marne (FR); Jean Delbe, Ville d'Avray (FR); Pierre Milhiet, Teyran (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 10/533,443

(22) PCT Filed: Oct. 29, 2003

(86) PCT No.: PCT/FR03/03231

§ 371 (c)(1), (2), (4) Date: Nov. 21, 2005

(87) PCT Pub. No.: WO2004/041859

PCT Pub. Date: May 21, 2004

(65) Prior Publication Data

US 2006/0153884 A1    Jul. 13, 2006

(30) Foreign Application Priority Data

Oct. 30, 2002    (FR)    .................... 02 13621

(51) Int. Cl.
*A61K 38/16*    (2006.01)
*A61K 38/17*    (2006.01)
*C12P 21/02*    (2006.01)
*C07K 14/745*    (2006.01)

(52) U.S. Cl. .................. 424/185.1; 435/69.1; 530/324

(58) Field of Classification Search .............. 424/185.1; 530/324, 300; 435/69.1
See application file for complete search history.

(56) References Cited

U.S. PATENT DOCUMENTS 5,461,029 A * 10/1995 Backer et al. .................. 514/2
6,103,880 A * 8/2000 Barritault et al. ............ 530/399
6,932,973 B2    8/2005 Barritault et al.

FOREIGN PATENT DOCUMENTS

FR    2 799 465    4/2001
WO    WO 02/083851    * 10/2002

OTHER PUBLICATIONS

Hampton et al, Molecular Biology of the Cell 3: 85-93, 1992.*
Bernard-Pierrot et al, J Biol Chem 277 (35): 32071-32077; Aug. 30, 2002.*
Zhang et al, J Biol Chem 274(9): 12959-12962, 1999.*
Ngo et al., The Protein Folding Problem and Tertiary Structure Prediction, pp. 491-495, 1994.*
Mason et al, Molecular Endocrinology 8(3): 325-332, 1994.*
Isabelle Bernard-Pierrot et al., "The Lysine-rich C-terminal Tail of Heparin Affin Regulatory Peptide is Required for Mitogenic and Tumor Formation Activities", Journal of Biological Chemistry, vol. 276, No. 15, Apr. 13, 2001, pp. 12228-12234.
Anil K. Chauhan et al., "Pleiotrophin transforms NIH 3T3 cells and induces tumors in nude mice", Proc. Natl. Acad. Sci. USA, vol. 90, Jan. 1993, pp. 679-682.
Rangana Choudhuri et al., "An Angiogenic Role for the Neurokines Midkine and Pleiotrophin in Tumorigenesis", Cancer Research, vol. 57, May 1, 1997, pp. 1814-1819.
Jose Courty et al., "Mitogenic Properties of a New Endothelial Cell Growth Factor Related to Pleiotrophin", Biochemical and Biophysical Research Communications, vol. 180, No. 1, Oct. 15, 1991, pp. 145-151.
Wenjing Fang et al., "Pleiotrophin Stimulates Fibroblasts and Endothelial and Epithelial Cells and is Expressed in Human Cancer", Journal of Biological Chemistry, vol. 267, No. 36, Dec. 25, 1992, pp. 25889-25897.
Soichi Kojima et al., "Synthetic Peptides Derived from Midkine Enhance Plasminogen Activator Activity in Bovine Aortic Endothelial Cells", Biochemical and Biophysical Research Communications, vol. 206, No. 2, Jan. 17, 1995, pp. 468-473.
Soichi Kojima et al., "Midkine Enhances Fibrinolytic Activity of Bovine Endothelial Cells", Journal of Biological Chemistry, vol. 270, No. 16, Apr. 21, 1995, pp. 9590-9596.
P. E. Milhiet et al., "Upregulation of the angiogenic factor heparin affin regulatory peptide by progesterone in rat uterus", Journal of Endocrinology, vol. 158, 1998, pp. 389-399.
Heikki Rauvala, "An 18-kd heparin-binding protein of developing brain that is distinct from fibroblast growth factors", EMBO Journal, vol. 8, No. 10, 1989, pp. 2933-2941.
Gerald E. Stoica et al., "Identification of Anaplastic Lymphoma Kinase as a Receptor for the Growth Factor Pleiotrophin", Journal of Biological Chemistry, vol. 276, No. 20, May 18, 2001, pp. 16772-16779.
Francis Vacherot et al., "Glycosaminoglycans Differentially Bind HARP and Modulate Its Biological Activitiy", Journal of Biological Chemistry, vol. 274, No. 12, Mar. 19, 1999, pp. 7741-7747.
Francis Vacherot et al., "Involvement of Heparin Affin Regulatory Peptide in Human Prostate Cancer", The Prostate, vol. 38, 1999, pp. 126-136.
Anton Wellstein et al., "A Heparin-binding Growth Factor Secreted from Breast Cancer Cells Homologous to a Developmentally Regulated Cytokine", Journal of Biological Chemistry, vol. 267, No. 4, Feb. 5, 1992, pp. 2582-2587.
Hsiu-Jeng Yeh et al., "Upregulation of Pleiotrophin Gene Expression in Developing Microvasculature, Macrophages, and Astrocytes after Acute Ischemic Brain Injury", Journal of Neuroscience, vol. 18, No. 10, May 15, 1998, pp. 3699-3707.

* cited by examiner

*Primary Examiner*—Phuong Huynh
(74) *Attorney, Agent, or Firm*—Young & Thompson

(57) ABSTRACT

The invention concerns peptide fragments 13-39 and 65-97 of the HARP factor, which inhibit angiogenesis. Advantageously, said peptides can be associated with the peptide 111-136 of HARP. The invention also concerns pharmaceutical compositions comprising said peptides or nucleic acids encoding said peptides, and their use for treating pathologies associated with an angiogenesis, in particular proliferative disorders such as cancer.

6 Claims, 4 Drawing Sheets

SEQUENCE LISTING

```
<160> NUMBER OF SEQ ID NOS: 7

<210> SEQ ID NO 1
<211> LENGTH: 136
<212> TYPE: PRT
<213> ORGANISM: Homo sapiens

<400> SEQUENCE: 1

Gly Lys Lys Glu Lys Pro Glu Lys Val Lys Lys Ser Asp Cys Gly
 1               5                  10                  15

Glu Trp Gln Trp Ser Val Cys Val Pro Thr Ser Gly Asp Cys Gly Leu
                20                  25                  30

Gly Thr Arg Glu Gly Thr Arg Thr Gly Ala Glu Cys Lys Gln Thr Met
            35                  40                  45

Lys Thr Gln Arg Cys Lys Ile Pro Cys Asn Trp Lys Lys Gln Phe Gly
        50                  55                  60

Ala Glu Cys Lys Tyr Gln Phe Gln Ala Trp Gly Glu Cys Asp Leu Asn
    65                  70                  75                  80

Thr Ala Leu Lys Thr Arg Thr Gly Ser Leu Lys Arg Ala Leu His Asn
                85                  90                  95

Ala Glu Cys Gln Lys Thr Val Thr Ile Ser Lys Pro Cys Gly Lys Leu
               100                 105                 110

Thr Lys Pro Lys Pro Gln Ala Glu Ser Lys Lys Lys Lys Glu Gly
           115                 120                 125

Lys Lys Gln Glu Lys Met Leu Asp
       130                 135

<210> SEQ ID NO 2
<211> LENGTH: 28
<212> TYPE: PRT
<213> ORGANISM: Homo sapiens

<400> SEQUENCE: 2

Ser Asp Cys Gly Glu Trp Gln Trp Ser Val Cys Val Pro Thr Ser Gly
 1               5                  10                  15

Asp Cys Gly Leu Gly Thr Arg Glu Gly Thr Arg Thr
                20                  25

<210> SEQ ID NO 3
<211> LENGTH: 33
<212> TYPE: PRT
<213> ORGANISM: Homo sapiens

<400> SEQUENCE: 3
```

-continued

```
Ala Glu Cys Lys Tyr Gln Phe Gln Ala Trp Gly Glu Cys Asp Leu Asn
 1               5                  10                  15

Thr Ala Leu Lys Thr Arg Thr Gly Ser Leu Lys Arg Ala Leu His Asn
                20                  25                  30

Ala

<210> SEQ ID NO 4
<211> LENGTH: 26
<212> TYPE: PRT
<213> ORGANISM: Homo sapiens

<400> SEQUENCE: 4

Lys Leu Thr Lys Pro Lys Pro Gln Ala Glu Ser Lys Lys Lys Lys
 1               5                  10                  15

Glu Gly Lys Lys Gln Glu Lys Met Leu Asp
                20                  25

<210> SEQ ID NO 5
<211> LENGTH: 84
<212> TYPE: DNA
<213> ORGANISM: Homo sapiens

<400> SEQUENCE: 5
tctgactgtg gagaatggca gtggagtgtg tgtgtgccca ccagtggaga ctgtgggctg    60
ggcacacggg agggcactcg gact                                          84

<210> SEQ ID NO 6
<211> LENGTH: 93
<212> TYPE: DNA
<213> ORGANISM: Homo sapiens

<400> SEQUENCE: 6
tgcaaatacc agttccaggc ctggggagaa tgtgacctga acacagccct gaagaccaga    60
actggaagtc tgaagcgagc cctgcacaat gcc                                93

<210> SEQ ID NO 7
<211> LENGTH: 75
<212> TYPE: DNA
<213> ORGANISM: Homo sapiens

<400> SEQUENCE: 7
ctgaccaagc ccaaacctca agcagaatct aagaagaaga aaaggaagg caagaaacag     60 gagaagatgc tggat                                                    75
```

PEPTIDE FRAGMENTS OF THE HARP FACTOR INHIBITING ANGIOGENESIS

This application is a 371 National Stage application of PCT/FR2003/003231, filed Oct. 29, 2003, and claims priority to French application No. 02/13621, filed Oct. 30, 2002.

The present invention relates to peptide fragments of the HARP protein which inhibit angiogenesis.

BACKGROUND OF THE INVENTION

Current cancer therapy is based on radiotherapy, surgery, sometimes very crippling and/or the use of anti-cancer drugs which block mitoses and which can be very aggressive, which sometimes limits their use. There is currently no universal therapy against this pathology. The role of angiogenesis in tumour growth has been the subject of intensive research and it is now accepted by all the scientific community that tumour growth cannot take place without angiogenesis. This mechanism is defined as a dynamic process induced by a certain number of angiogenic factors of which the principal ones are: vascular endothelial growth factor (VEGF), fibroblast growth factor (FGF) or heparin affin regulatory peptide (HARP) which in several cases are overexpressed by the tumours themselves. Since a tumour cannot develop without neovascularisation, the suppression or the inhibition of the angiogenic factors must lead to a regression of the tumour growth regardless of the type of tumour. Nowadays in the treatment of cancer or of proliferative diseases several companies are developing an anti-angiogenesis strategy based for example either on inhibitors of angiogenic factors (or of receptors thereof when these are identified), or by inducing vascular micro-thromboses using the endothelial cell as anchorage for catalysts of the thrombosis, or even by using peptide agents which inhibit angiogenesis by mechanisms as yet unidentified. These approaches have not yet produced clear results and it appears that the inhibitors based on blocking one single angiogenesis pathway induce aggravating rebound effects. These results are currently leading these companies to propose cocktails of inhibitors which make it possible to hope for radical simultaneous destruction of the vessels and tumour cells.

The angiogenic role of the HARP factor has been demonstrated through a number of experiments conducted in vitro and in vivo (Papadimitriou et al 2001; Papadimitriou et al, 2000). Thus in an in vitro model in which endothelial cells are seeded on a collagen gel it has been shown that HARP is capable of inducing the formation of pseudo-capillaries, thus mimicking the first stages of angiogenesis, that is to say the activation of the endothelial cells and their migration through a partially destroyed extracellular matrix. Reinforcing this observation, a synthetic peptide of 43 amino acids corresponding to a part of the C-terminal domain of HARP is capable of stimulating the secretion of the plasminogen activator by bovine aortic endothelial cells (ABAE) and inhibiting the secretion of its inhibitor PAI-1 (Kojima et al, 1995a; Kojima et al, 1995b). This activator induces the cleavage of the plasminogen in plasmin, a protease which plays a key role in the degradation of the extracellular matrix. HARP shares this characteristic with another protein which binds to heparin (Matsubara et al, 1990): the protein midkine (MK) which exhibits 50% homology of amino acid sequence with which it constitutes a new family of HBGF (Tsutsui et al, 1991).

The role played by HARP in tumoral angiogenesis has also been underlined by Roy Bicknell's team. Thus the overexpression of HARP in the MCF7 mammary carcinoma cells injected into "nude" mice results in an increase in the size of the tumour relative to those obtained without overexpression. The increase in the size of the tumour is linked to the vascular density and to a multiplication of the endothelial cells (Choudhuri et al, 1997). The proliferation of the endothelial cells is another key stage in angiogenesis in which HARP could play a crucial role. In fact, since 1991 it has been shown that HARP stimulated the proliferation of the endothelial cells in vitro (Courty et al, 1991). This mitogenic activity could be demonstrated in other models: HARP stimulates in vitro the formation of colonies of non-tumorigenic epithelial cells SW13 (Fang et al, 1992) in soft agar and the overexpression of its cDNA in NIH 3T3 cells (Chauhan et al, 1993) or SW-13 cells (Fang et al, 1992) induces the formation of a tumour in the "nude" mouse. This mitogenic role is reinforced by the expression of the molecule in numerous cancers. By the use of RNAse protection tests and/or the Northern blot technique, HARP mRNA was detected in the cell lines coming from breast cancer (T47 Dco, MDA-MB231, MDA-MB361, Hs-578T) (Fang et al, 1992), ovarian cancer (A1827, PA-1) (Riegel et al, 1994), prostate cancer (PC-3) (Vacherot et al, 1999a) and lung cancer (Jager et al, 1997).

In vivo, in different tissue models the localisation of HARP is in particular associated with the endothelial cells of the blood capillaries. mRNA for HARP protein was demonstrated in the endothelial cells belonging to the blood capillaries of human prostate and mammary glands (Vacherot et al, 1999a; Ledoux et al, 1997). In the rat uterine model there was also demonstrated an increase in the rate of mRNA and of HARP protein associated with the progestative phase of the cycle. This result was confirmed by the injection of progesterone into ovariectomised rats. The overexpression induced by the progesterone is detectable in the capillary endothelial cells of the endometrium (Milhiet et al, 1998). The presence of the HARP protein on the surface of the endothelial cells has also been demonstrated indirectly during intravenous injections of heparin in humans (Novotny et al, 1993). Recently the Deuel group demonstrated an increase in the expression of the mRNA of HARP in the microvessels in development after a cerebral ischaemia in the rat (Yeh et al, 1998). The growth factors HARP and midkine (MK) are molecules which exhibit 50% homology and possess mitogenic properties on epithelial, fibroblastic and endothelial cells. The expression of each of these growth factors (mRNA, protein) was demonstrated in human tumours of varied origin (breast, lung, ovary, neuroblastoma, stomach, colon), suggesting their potential role in the course of the tumoral progression. A few clinical studies have evaluated the coexpression of HARP and of MK and in particular the blood level of these angiogenic molecules in patients with tumours. Recently an immunological dosage for these two molecules has been developed based on their affinity for heparin. The sensitivity of the method is 80 pg/ml for HARP and 40 pg/ml for MK (Stoica et al, 2001).

U.S. Pat. No. 5,641,743 and U.S. Pat. No. 6,103,880 describe in a general manner the HARP protein and the use of this protein to stimulate angiogenesis.

The Patent Application FR 2 799 465 discloses a fragment of HARP with angiogenic activity.

In fact it has been shown that the angiogenic activity of HARP occurred through a smaller peptide. Thus a consensus sequence of 18 amino acids resulting from the HARP peptide sequence but also found on a large number of angiogenic factors possessed an angiogenic activity by itself.

Like the majority of the growth factors, the mechanism of action of HARP is brought about by an interaction with a membrane receptor with high affinity tyrosine kinase activity ($K_D$=50 pM) known as "anaplastic lymphoma kinase" or ALK (Stoica et al, 2001).

Furthermore, the biological activity of HARP, like the majority of HBGFs, also depends upon its interaction with glycoaminoglycans or GAG, of the heparan or chondroitin sulphate type (Vacherot et al, 1999b).

Thus the mitogenic activity of HARP is potentiated in the presence of heparin, heparan sulphate and chondroitin sulphate of type A and B. Cellular treatment with heparinase abolishes the mitogenic activity of HARP. This activity can then be restored in the presence of heparin. A study relating to the relationships between the structure and the function of HARP has suggested that the C-terminal part of HARP corresponding to the amino acid residues 111-136 (numbering with reference to the form $HARP_{136}$) is directly implicated in the induction of the mitogenic activity (Bernard-Pierrot et al, 2001) and in its interaction with the receptor ALK. Moreover it has been established that the peptide 111-136 is neither mitogenic n or angiogenic and that the HARP molecule from which the amino acids 111-136 have been deleted specifically inhibits the biological activity of HARP whilst having negative dominant effects with regard to HARP (Bernard-Pierrot et al 2002).

BRIEF SUMMARY OF THE INVENTION

The inventors have now demonstrated in a surprising manner that the angiogenic HARP factor contains peptide fragments capable of inhibiting angiogenesis as well as tumour growth.

This relates to all or part of the amino acid sequences 13-39 and 65-97 localised in the domains in the beta sheet of HARP.

These fragments are therefore of particular interest for inhibiting angiogenesis and tumour growth and consequently can be put to use in the treatment of proliferative disorders such as cancer or pathologies for which an excessive angiogenesis is observed, that is to say for example diabetic retinopathy.

According to a preferred embodiment of the invention it is proposed to associate one and/or other of these peptides with a peptide corresponding to all or part of the sequence 111-136 of HARP. This association offers the advantage of avoiding the "rebound effect" observed with the other techniques for inhibition of certain angiogenic factors. In fact, it appears that the inhibition in vivo of an angiogenic factor is compensated for by the activation of another angiogenic factor.

In the present invention, the peptides 13-39 or 65-97 act on the GAG receptors, which are low affinity receptors inhibiting the angiogenic activity of HARP, whilst the peptide 111-136 acts on the high affinity ALK receptor.

The blockage of the high affinity HARP sites as well as the low affinity ones common to other angiogenic factors permits a particularly effective therapy in the treatment of the pathologies associated with a phenomenon of angiogenesis.

The proposed therapeutic approach consists of an administration of peptides or an administration of nucleic acids which code for these peptides.

BRIEF DESCRIPTION OF THE DRAWINGS

FIG. 6 represents the inhibition by the HARP peptides 13-39 and 65-97 of the angiogenesis induced by HARP in an in vivo model. Three hundred microlitres of Matrigel® incubated with 5 nM of HARP in the presence or absence of the HARP peptides 13-39 and 65-97 used at a concentration of 1 µM are injected subcutaneously into a mouse. The control of the experiment is achieved using FGF-2. Seven days later the mice are sacrificed and the Matrigel® is removed. Sections having a thickness of 8 µM are produced. The sections are then stained with Trichrome from Gomori. The number of cells which have invaded the Matrigel® is quantified by image analysis with NIH software. The results represent the

DETAILED DESCRIPTION OF THE INVENTION

The HARP Factor and its Fragments

Figure 1:
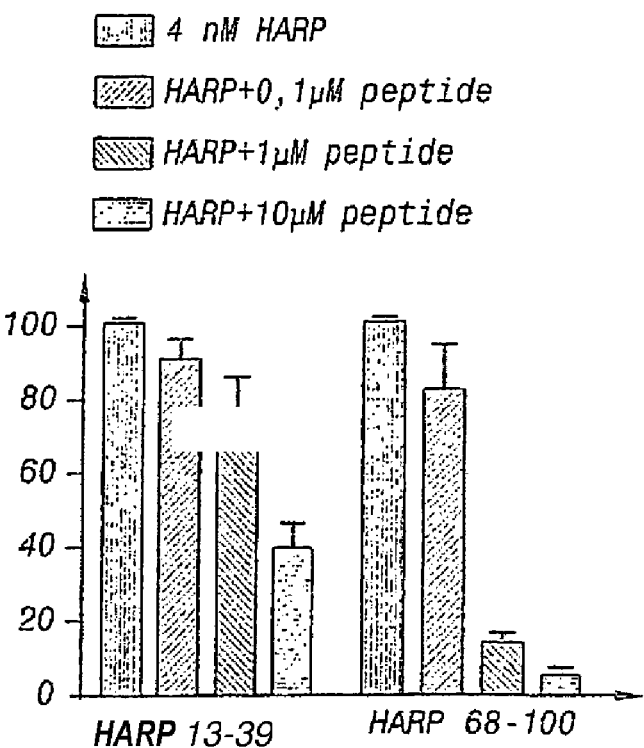
FIG. 1 shows a graph representing the inhibition of the cellular proliferation induced by HARP. NIH 3T3 cells are or are not stimulated by 4 nM of HARP in the presence or absence of peptide 13-39 or 65-97 used in a concentration of from 0.1 µM to 10 µM. After 24 hours' incubation the cellular proliferation is estimated by measurement of the tritiated thymidine incorporated by the cells.
Figure 2:
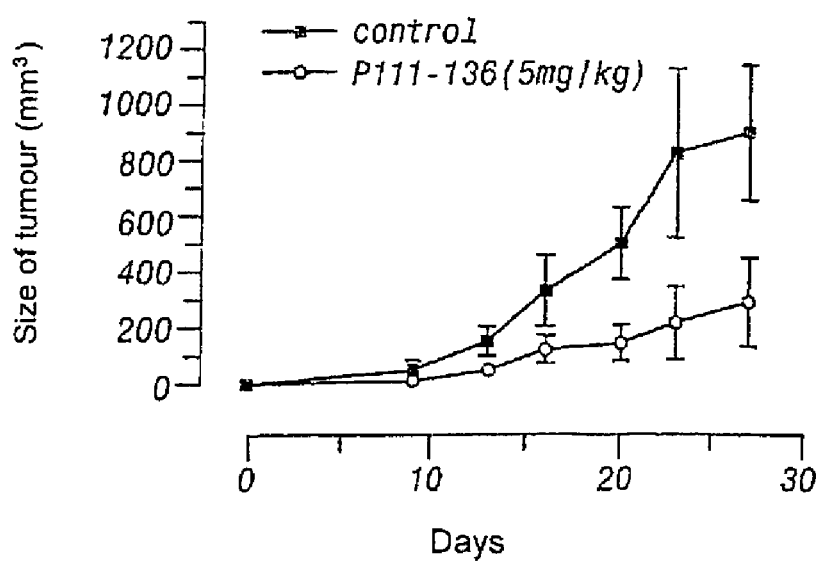
FIG. 2 shows a graph which represents the inhibition of tumour growth in a nude mouse model having received an injection of PC3 cells (line resulting from prostate cancer). Two million PC3 cells are injected into groups of 5 nude mice treated or not by daily injection in the region of the tumour with PBS (control) or with the HARP peptide 111-136 at a concentration of 5 mg/kg. The tumour growth for each group of animals is evaluated by measurement of the size of the tumour on day 9, 13, 16, 20, 23 and 27.

The "heparin affin regulatory peptide" or HARP (Courty et al, 1991) also called "pleiotrophin" (Welistein et al, 1992) or "heparin binding-growth associated molecule" or HB-GAM (Rauvala et al, 1989) belongs to the family of "heparin binding growth factors" (HBGF). The human peptide sequence and the corresponding human gene are accessible on the database (Genbank n° X52946).

The HARP protein is synthesised in the form of a precursor of 168 amino acids which possesses two cleavage sites by the peptidase signal leading to a mature protein of 136 or 139 amino acids ($HARP_{136}$ or $HARP_{139}$). The mature forms $HARP_{136}$ and $HARP_{139}$ possess the same biological activities in vitro, nevertheless the specific activity of induction of the cellular proliferation of the form $HARP_{139}$ is better than that observed for the form $HARP_{136}$ (Bernard Pierrot et al, 2001).

The numbering of the amino acids is given as a function of the HARP protein of 136 amino acids.

The human peptide sequence of $HARP_{136}$ is also presented in sequence SEQ ID NO: 1.

In the context of the present invention, the HARP protein or its fragments refers to the human protein or its fragments, but also to any variant of the protein in other species, particularly in mammals of the bovine, rodent type, etc. Thus the sequences of mice (Genbank N° AK017768 or NM 008973), rat (Genbank N° NM017066), ox (Genbank N° X52945) are available. Variants are also known in Zebrafish (Genbank N° NM131070) and in *Drosophila* (miple protein Genbank N° NM 138178).

It has been demonstrated that units of homology with thrombospondin of type TSR1 (thrombospondin repeat type 1), present in the domains in the beta sheet of HARP, particularly in the region of the amino acids contained in the two peptides 13-39 and 65-97, are implicated in the fixation of HARP to heparin (Kilpelainen et al, 2000). These peptides in fact bind to the low affinity receptors of type GAG.

In a preferred manner, the fragments 13-39, 65-97 or 111-136 are the fragments as enumerated in the sequence SEQ ID NO: 1, namely the sequences:

```
13-39:
SDCGEWQWSVCVPTSGDCGLGTREGTRT        (SEQ ID NO: 2)

65-97:
AECKYQFQAWGECDLNTALKTRTGSLKRALHNA   (SEQ ID NO: 3)

111-136:
KLTKPKPQAESKKKKKEGKKQEKMLD.         (SEQ ID NO: 4)
```

Any peptide which is a "variant", "homologue" or "derivative" of these peptides, and which exhibits the same biological activity as these peptides, also forms part of the invention.

"Biological activity" is understood here to mean in particular an angiogenesis inhibiting activity. The antiangiogenic activity of a compound can easily be evaluated in vitro or in vivo by the person skilled in the art, particularly by means of the following tests:

- in vitro, by bringing peptides into contact with endothelial cells on collagen, and observation of the inhibition of the formation of capillaries;
- in vivo, by injection of matrix of the Matrigel® type, and observation of the inhibition of the formation of capillaries within the matrix;
- or depositing the peptide on a chorioallantoic membrane of an egg (of a chicken for example), and observing the effect of this peptide on the vascularisation of this membrane.

The observation of the endothelial cells (and consequently of the capillaries) can be carried out by specifically labelling these cells, for example by means of CD131 or lectin.

The biological activity of the peptides 13-39 and 65-97 also refers to their capacity to bind to the GAGs of the heparan or chondroitin sulphate type. The biological activity of the peptide 111-136 also refers to its capacity to bind to the ALK receptor.

The "variant", "homologue" or "derivative" peptides are defined as comprising the sequences similar to at least 70%, preferably at least 80%, more preferably at least 90%, even at least 95%, of the reference sequence.

These peptides can also be defined as comprising the sequences coded by a nucleic acid sequence which hybridises with the reference sequence or its complementary sequence under strict hybridisation conditions.

The term "similar" refers to the perfect resemblance or identity between the amino acids compared but also to the imperfect resemblance which is defined as similarity. This search for similarities in a polypeptide sequence takes into account the conservative substitutions which are substitutions of amino acids of the same class, such as substitutions of amino acids with uncharged side chains (such as asparagine, glutamine, serine, threonine, and tyrosine), amino acids with basic side chains (such as lysine, arginine and histidine), amino acids with acidic side chains (such as aspartic acid and glutamic acid); amino acids with apolar side chains (such as glycine, alanine, valine, leucine, isoleucine, proline, phenylalanine, methionine, tryptophan and cysteine).

More generally, "variant, homologue or derivative amino acid sequence" is therefore understood to mean amino acids which differ from the reference sequence by substitution, deletion and/or insertion of an amino acid or a plurality of amino acids, preferably a reduced number of amino acids, particularly by substitution of natural amino acids by non-natural amino acids or pseudo-amino acids at positions such that these modifications do not significantly undermine the biological activity of the peptides.

The homology is generally determined using sequence analysis software (for example, Sequence Analysis Software Package of the Genetics Computer Group, University of Wisconsin Biotechnology Center, 1710 University Avenue, Madison, Wis. 53705). Sequences of amino acids which are similar are aligned in order to obtain the maximum degree of homology (i.e. identity or similarity, as defined above). For this purpose it may be necessary to introduce gaps into the sequence in an artificial manner. Once the optimal alignment is achieved, the degree of homology is established by recording all of the positions for which the amino acids of the two sequences compared are identical with respect to the total number of positions.

The "variant", "homologue" or "derivative" peptides have the same length as the reference sequences.

The fragments of SEQ ID NO: 2 and SEQ ID NO: 3 containing respectively the unit 18-23 WQWSVC (Residues 6-11 of SEQ ID NO: 2) or the unit 71-77 FQAWGEC (Residues 7-13 of SEQ ID NO: 3) are of particular interest.

According to the invention, the peptides can moreover be modified chemically or enzymatically in order to improve their stability or their bioavailability.

In a non-limiting manner, one or more of the lysine (K) amino acids of the peptides can for example be modified, particularly by:

- amidation: this modification is simple to accomplish, the positive charge of the lysine being substituted by hydrophobic groups (for example acetyl or phenylacetyl);
- amination: by formation of secondary amides from the primary amine R=$(CH_2)_4$-$NH_3^+$, for example by forming N-methyl, N-allyl or N-benzyl groups;
- or even by formation of N-oxide, N-nitroso, N-dialkyl phosphoryl, N-sulphenyl or N-glycoside groups.

Moreover it is possible in addition or alternatively to modify one or more threonine (T) and/or serine (S) amino acids of the peptides, particularly by introducing an ester or ether group at the position of the OH group of the side chain of the threonine and/or of the serine. Esterification, a simple operation, can be carried out with the aid of a carboxylic acid, an anhydride, by bridging, etc., in order to form acetates or benzoates for example. Etherification, which gives more stable compounds, can be effected with the aid of an alcohol, a halide, etc., in order to form a methyl ether or an O-glycoside for example.

Moreover it is possible in addition or alternatively to modify one or more glutamine (Q) amino acids for example by amidation, by forming secondary or tertiary amines, particularly with groups of the methyl and/or ethyl type, which may or may not be functionalised.

Moreover it is possible in addition or alternatively to modify one or more glutamate (E) and/or aspartate (D) amino acids, for example:

- by esterification, in order to form substituted or non-substituted methyl esters, ethyl esters, benzyl esters, thiols (activated esters), etc.,
- by amidation, particularly in order to form N,N dimethyl groups, nitroanilides, pyrrolidinyls, etc.

On the other hand it is preferable not to modify the proline amino acids which participate in the secondary structure of the peptides, in the knowledge furthermore that the amino acids G, A and M do not generally offer possibilities for modification which would be of obvious interest.

Production of the Peptides

The polypeptides which are useful in the present invention can be synthesised by any method well known to the person skilled in the art. The peptide according to the invention can for example be synthesised by chemical synthesis techniques, such as synthesis of the Merrifield type which is advantageous for reasons of purity, antigenic specificity, absence of unwanted secondary products and for its ease of production.

A recombinant peptide can also be produced by a process in which a vector containing a nucleic acid coding for the peptide is transferred into a host cell which is cultured in conditions which permit the expression of the corresponding peptide.

The peptide produced can then be recovered and purified.

The purification processes used are known to the person skilled in the art. The recombinant peptide obtained can be purified from lysates and cell extracts, from the supernatant of the culture medium, by methods used individually or in combination, such as fractionation, chromatography methods, immunoaffinity techniques with the aid of specific mono- or polyclonal antibodies, etc.

The nucleic acid which is useful for the production of recombinant peptide can in particular have the following sequences:

sequence coding for the peptide 13-39 (SEQ ID NO: 5)
sequence coding for the peptide 65-97 (SEQ ID NO: 6)
sequence coding for the peptide 111-136 (SEQ ID NO: 7).

The nucleic acids which code for "variant", "homologue" or "derivative" peptides of the HARP peptides described above also form part of the invention.

These nucleic acids can be defined as comprising:

i) sequences similar to at least 70%, preferably at least 80%, preferably at least 90%, even at least 95% of the sequence SEQ ID NOS:5, 6 or 7; or
ii) sequences which hybridise with the sequence SEQ ID NOS: 5, 6 or 7 or its complementary sequence under strict hybridisation conditions, or
iii) sequences which code for the reference peptide as defined above.

In a preferred manner, such a homologous nucleotide sequence hybridises specifically with the complementary sequences of the sequence SEQ ID NOS: 5, 6 or 7 under strict conditions. The parameters defining the conditions of strictness depend upon the temperature at which 50% of the paired strands separate (Tm).

For the sequences comprising more than 30 bases, Tm is defined by the relation: Tm=81.5+0.41 (% G+C)+16.6 Log (concentration of cations)−0.63 (% formamide)−(600/number of bases) (Sambrook et al, 1989).

For the sequences with a length less than 30 bases, Tm is defined by the relation: Tm=4(G+C)+2(A+T).

Under appropriate strict conditions, in which the aspecific sequences do not hybridise, the hybridisation temperature can preferably be 5 to 10° C. below Tm, and the hybridisation buffers used are preferably solutions with a high ionic force such as a solution 6×SSC for example.

The term "similar sequences" employed above refers to the perfect resemblance or identity between the nucleotides compared but also to the imperfect resemblance which is referred to as similarity. This search for similarities in the nucleic sequences distinguishes for example the purines and the pyrimidines.

Therefore a homologous nucleotide sequence includes any nucleotide sequence which differs from the sequence SEQ ID NOS: 5, 6 or 7 by mutation, insertion, deletion or substitution of one or more bases, or by the degeneracy of the genetic code, in so far as it codes for a peptide having the biological activity of the fragments of HARP to which 10 they refer.

The nucleic acid sequence of interest can be inserted into an expression vector in which it is linked in an operative manner to an element or elements permitting its expression or the regulation of its expression, such as in particular transcription promoters, 15 activators and/or terminators.

The signals controlling the expression of the nucleotide sequences (promoters, activators, termination sequences . . . ) are chosen as a function of the host cell used. For this purpose the nucleotide sequences according to the invention can be inserted into vectors which can replicate autonomously within the chosen host, or vectors integrated into the chosen host. Such vectors will be prepared according to the methods currently used by the person skilled in the art, and the clones resulting therefrom can be introduced into an appropriate host by standard methods, such as for example electroporation or precipitation with calcium phosphate.

The cloning and/or expression vectors such as are described above containing a nucleotide sequence defined according to the invention also form part of the present invention.

The invention further relates to the host cells transfected in a transitory or stable manner by these expression vectors. These cells can be obtained by the introduction into prokaryotic or eukaryotic host cells of a nucleotide sequence inserted into a vector as defined above, then the culturing of the said cells under conditions which permit the replication and/or the expression of the transfected nucleotide sequence.

Examples of host cells include in particular cells of mammals, such as the cells COS-7,293, MDCK, cells of insects such as the cells Sf9, of bacteria such as *E. coli* and of strains of yeasts such as L40 and Y90.

Gene Therapy

According to a particular embodiment of the invention, a gene therapy is implemented. It involves administering to a patient a nucleic acid which codes for the peptide or peptides of interest, under conditions such that the peptide or peptides is/are expressed in vivo by the cells of the patient into which the nucleic acid has been transferred.

The nucleic acid administered comprises a nucleotide sequence as defined above in the section "Production of the peptides".

Such a nucleic acid can be in particular in the form of a vector of DNA, for example a plasmid vector. One or more vectors can be administered, each vector being capable of carrying one or more sequence(s) coding for at least one of the peptides of interest, namely the peptide 13-39, 65-97 or 111-136.

According to a preferred embodiment, a vector is used bearing a sequence coding for the peptide 13-39, another vector bearing a sequence coding for the peptide 65-97 and possibly finally another vector comprising a sequence coding for the peptide 111-136.

The vector or vectors of DNA can be introduced in vivo by any technique known to the person skilled in the art. In particular, it is possible to introduce the vector of DNA in vivo in a naked form, that is to say without the aid of any vehicle or system which would facilitate the transfection of the vector in the cells (EP 465 529).

A gene gun can also be employed, for example by depositing the DNA on the surface of "gold" particles and by projecting these in such a way that the DNA penetrates through the skin of a patient (Tang et al, 1992). Injections by means of a liquid gel are equally possible for simultaneously transfecting the skin, muscle, fatty tissue and mammary tissue (Furth et al, 1992; Robinson et al, 1997).

Techniques of microinjection, electroporation, precipitation with calcium phosphate, formulations with the aid of nanocapsules or of liposomes are other techniques which are available.

Biodegradable polyalkyl cyanoacrylate nanoparticles are particularly advantageous. In the case of liposomes, the use of cationic lipids favours the encapsulation of the nucleic acids which are negatively charged and facilitates the fusion with the negatively charged cell membranes.

Alternatively the vector can be in the form of a recombinant virus comprising, inserted in its genome, a nucleic acid sequence which codes for the said peptide(s).

The viral vector can preferably be chosen from amongst an adenovirus, a retrovirus, in particular a lentivirus, as well as an adeno-associated virus (AAV), a herpes virus, a cytomegalovirus (CMV), a vaccinia virus, etc.

Lentivirus vectors have been described for example by Firat et al, (2002).

In an advantageous manner, the recombinant virus is a defective virus. The term "defective virus" designates a virus incapable of replicating itself in a target cell. Generally the genome of the defective viruses is stripped of at least the sequences necessary for the replication of the said virus in the infected cell. These regions can either be eliminated, or rendered non-functional or even substituted by other sequences and in particular by the nucleic acid which codes for the peptide of interest. Nevertheless, in spite of everything the defective virus preferably retains all the sequences of its genome which are necessary for the encapsulation of the viral particles.

A targeted administration of genes is for example described in the application WO 95/28 494.

Pathologies Concerned

The peptides according to the invention exhibit properties of inhibition of angiogenesis.

For this reason these peptides or the nucleic acids expressing these peptides are particularly useful for the treatment of various pathologies associated with an angiogenesis or which give rise to angiogenic factors.

"Treatment" is understood to mean treatment for a curative purpose (aimed at least at alleviating or stopping the development of the pathology) or a prophylactic purpose (aimed at reducing the risk of the pathology appearing).

The pathologies concerned include but are not limited to:

Proliferative disorders. These are understood to mean any abnormal proliferation of cells, whether benign or malignant. These tumours include melanomas, carcinomas, sarcomas, rhabdomyosarcoma, retinoblastoma, neuroblastoma, osteosarcoma. Amongst the solid tumours mention may be made in particular of tumours (primitive or not) of the breast, the ovary, the lung, the cervix, the digestive tract, in particular the colon, the urologic system, the liver, the pancreas, the bones. Non-solid tumours are equally covered, namely in particular leukaemias or lymphomas.

The proliferative disorders can be treated at any stage in the proliferation. The peptides or the nucleic acids according to the invention are in particular useful for combating the development of tumoral metastases. Amongst the benign tumours mention may finally be made in particular of haemangiomas and hepatocellular adenomas.

The therapeutic antiangiogenic effect of the peptides of the invention is materialised in these applications in particular by an effect of inhibition of the growth of the tumour.

Ocular lesions, which include in particular pathologies of the retina such as diabetic retinopathy, macular degeneration, occlusion of the renal vein or artery, glaucoma, etc. The peptides or nucleic acids of the invention can also be useful for treating ocular lesions which may be the consequence of surgical repair work such as corneal grafting.

rheumatoid polyarthritis, which is an in flammatory disease associated with an intense angiogenesis (Jackson et al, 1988).

and skin diseases such as psoriasis.

The peptides of the invention can also be useful as abortive compounds, for the control of births, by blocking uterine angiogenesis and therefore the implantation of the embryo.

Pharmaceutical Compositions

The invention therefore relates to a pharmaceutical composition comprising, as active substance, at least one HARP peptide 13-39 or 65-97, or a peptide derived from one of these with one or more pharmaceutically acceptable excipients.

The invention further relates to a pharmaceutical composition comprising, as active substance, a nucleic acid which comprises a sequence coding for at least one HARP peptide 13-39 or 65-97, or a peptide derived from one of these, linked in an operative manner to one or more element(s) permitting the expression of the peptide or the regulation of its expression, with one or more pharmaceutically acceptable excipients.

It is understood that the sequence is optionally linked in an operative manner to one or more element(s) permitting the expression of the peptide or the regulation of its expression.

"Excipient" or "pharmaceutically acceptable vehicle" is understood to mean any solvent, dispersion medium, absorption-retarding agents etc., which do not produce a secondary reaction, for example an allergic reaction, in humans or animals.

According to a preferred embodiment of the invention at least one of the peptides 13-39, 65-97, or of their derivative peptides is associated with the HARP peptide 111-136 or with a derived peptide.

Therefore the invention also provides a pharmaceutical composition comprising at least one HARP peptide 13-39 or 65-97, or a peptide derived from one of these in association with a HARP peptide 111-136 or a derived peptide in the presence of one or more pharmaceutically acceptable excipients.

A preferred pharmaceutical composition comprises:
the peptide 13-39 of sequence SEQ ID NO: 2;
the peptide 65-97 of sequence SEQ ID NO: 3; and
the peptide 111-136 of sequence SEQ ID NO: 4.

In an alternative or combined manner the invention also provides a pharmaceutical composition comprising a nucleic acid which comprises a sequence coding for a HARP peptide 13-39 or 65-97 or a peptide derived from one of these, the sequence being linked in an operative manner to one or more element(s) permitting its expression, in association with a nucleic acid which comprises a sequence coding for a HARP peptide 111-136 or a derived peptide, in the presence of one or more pharmaceutically acceptable excipients.

It is understood that the sequence(s) is/are optionally linked in an operative manner to one or more element(s) permitting the expression of the peptide(s) or the regulation of the expression thereof.

A preferred composition comprises:
a nucleic acid coding for the peptide 13-39 of sequence SEQ ID NO: 2;
a nucleic acid coding for the peptide 65-97 of sequence SEQ ID NO: 3;
a nucleic acid coding for the peptide 111-136 of sequence SEQ ID NO: 4.

The nucleic acids can be carried by one single vector or can be in the form of separate vectors.

Another embodiment of the invention includes the substantially simultaneous administration of separate compositions comprising on the one hand at least one HARP peptide 13-39 or 65-97 or a peptide derived from one of these or a nucleic acid coding for one of these peptides and on the other hand a HARP peptide 111-136 or a derived peptide or a nucleic acid coding for these peptides.

The administration can also be carried out in a sequential manner by means of separate compositions comprising on the one hand at least one HARP peptide 13-39 or 65-97 or a peptide derived from one of these or even a nucleic acid coding for one of these peptides and on the other hand a HARP peptide 111-136 or a derived peptide or a nucleic acid coding for these peptides.

At least one HARP peptide 13-39 or 65-97 or a peptide derived from one of these or even a nucleic acid coding for one of these peptides and a HARP peptide 111-136 or a derived peptide or a nucleic acid coding for these peptides can therefore be individually administered in a pharmaceutically acceptable form.

The posology naturally depends upon the active substance under consideration, the mode of administration, the therapeutic indication, the age of the patient and the condition of the patient.

The dose of peptide is preferably from 0.1 to 250 mg/kg per day, preferably from 1 to 100 mg/kg per day.

The unit dose of the compound of formula (I) preferably comprises from 12.5 to 200 mg of this compound.

When the pharmaceutical compositions comprise nucleic acids, the doses of nucleic acid (sequence or vector) to be administered are also adapted a s a function in particular of the mode of administration, the targeted pathology as well as the duration of treatment. In general when recombinant viruses are used, these are formulated and administered in the form of doses of approximately $10^4$ to $10^{14}$ pfu/ml, preferably $10^6$ to $10^{10}$ pfu/ml. The term "pfu" (plaque-forming unit) corresponds to the infectivity of a viral solution and can be determined by infecting an appropriate cell culture and measuring, generally after 48 hours, the number of plaques of infected cells. The techniques for determining the pfu content of a viral solution are well described by the literature.

The pharmaceutical compositions according to the invention can be formulated in such a way as to be administered to the patient by one single route or by different routes.

When administration by the parenteral route is envisaged, more particularly by injection, the compositions according to the invention comprising the active substance(s) are present in the form of injectable solutes and suspensions packed in ampoules or phials for slow perfusion. The injection can in particular be carried out by the subcutaneous, intramuscular or intravenous route.

In a preferred manner, particularly in the case of a solid tumour, the pharmaceutical composition can be injected at the actual site of the angiogenesis.

In the case of administration by the oral route, the compositions according to the invention are present in the form of capsules, effervescent tablets, coated or uncoated tablets, sachets, sugar-coated pills, ampoules or drinkable solutes, microgranules or prolonged-release forms.

The forms for parenteral administration are obtained in a conventional manner by mixing the active substance(s) with buffers, stabilising agents, preservatives, solubilising agents, isotonic agents and suspension agents. In accordance with known techniques, these mixtures are then sterilised then packaged in the form of intravenous injections.

The person skilled in the art will be able to use by way of buffer those buffers which are based on organic phosphate salts.

Examples of suspension agents encompass methylcellulose, hydroxyethylcellulose, hydroxypropylcellulose, acacia and sodium carboxymethylcellulose.

Furthermore, useful stabilisers according to the invention are sodium sulphite and sodium metasulphite, whilst mention may be made of sodium p-hydroxybenzoate, sorbic acid, cresol and chlorocresol by way of preservatives. For the preparation of oral solution or suspension the active substances are dissolved or suspended in an appropriate vehicle with a dispersing agent, a humectant agent, a suspension agent (for example polyvinylpyrrolidone), a preservative (such as methylparaben or propylparaben), a taste-correcting agent or a colouring.

For the preparation of microcapsules, the active substances are combined with appropriate diluents, appropriate stabilisers, agents favouring the slow release of the active substances or any other type of additive for the formation of a central core which is then coated with an appropriate polymer (for example, a water-soluble resin or a resin which is insoluble in water). The techniques known to the person skilled in the art will be used for this purpose.

The microcapsules thus obtained are then, if need be, formulated in appropriate dosage units.

Administration by the ocular route can also be envisaged, in particular in the case of treatment of an ocular lesion.

The pharmaceutical composition according to the invention is then in the form of an ophthalmic composition for local administration in the eye, for example, as an eye wash, or an ophthalmic cream.

The ophthalmic composition can be an aqueous solution comprising distilled water, or a physiological saline solution in which the peptides according to the invention are dissolved. A given number of additives can be incorporated in the ophthalmic composition if necessary, for example, buffer agents, agents ensuring isotonicity with tears, preservatives, thickeners, stabilisers, antioxidants, pH-adjusting agents, chelating agents, etc.

The eye drops are prepared by aseptic manipulation or sterilisation is carried out at an appropriate stage in the preparation.

The ophthalmic creams can be prepared in an aseptic manner by mixing the active substance with a usual base. The bases for ophthalmic creams are, for example, vaseline, jelene 50 or plastibase, macrogol, etc. Surfactants can be added in order to increase hydrophilia. Additives such as those described above, for example, preservatives, can be added if necessary.

In general, for local ophthalmic application a satisfactory effect in the adult is obtained by the administration of a droplet in the eye of a preparation containing from 0.001 to 10%, preferably 0.01 to 1% weight/volume of the compound according to the invention or of a pharmaceutically acceptable salt thereof several times, preferably one to six times per day, and each time with preferably one to four droplets per eye, and in the case of use of an ophthalmic cream, a preparation containing 0.001 to 10%, preferably 0.01 to 1% weight/volume of the compound according to the invention or of a pharmaceutically acceptable salt thereof, with application preferably one to six times per day in the eye.

The peptides according to the invention can also be formulated in the form of liposomes. The liposomes are formed from phospholipids which are dispersed in an aqueous medium and spontaneously form multilamellar concentric two-layer vesicles. These vesicles generally have a diameter of from 25 nm to 4 μm and can be subjected to sonic treatment, leading to the formation of smaller unilamellar vesicles with a diameter of from 200 to 500 Å, containing an aqueous solution at their core.

Liposomes can be particularly advantageous for administering the medicament to a precise cell or tissue target. For this, the lipids can be coupled chemically to targeting molecules, such as targeting peptides (for example hormones), or antibodies.

The present invention also relates to the use of at least one HARP peptide 13-39 or 65-97, or a peptide derived from one of these, possibly in association with a HARP peptide 111-136 or a derived peptide, for the preparation of a medicament intended to inhibit the angiogenesis or intended for the treatment of a pathology associated with an angiogenesis.

The pathologies concerned are as mentioned above.

The invention further relates to a method of inhibiting angiogenesis or for treating a pathology associated with an angiogenesis in a mammal, more particularly a human, comprising the administration in this mammal of a therapeutically effective quantity of at least one HARP peptide 13-39 or 65-97, or a peptide derived from one of these, optionally in association with a HARP peptide 111-136 or a peptide derived therefrom.

Naturally, the peptides according to the invention or nucleic acids can be used alone or in association with any other active substance. Mention may be made in particular of the peptide 150-183 of amphoterin, which inhibits the formation of metastases (Taguchi et al, 2000; Huttunen et al, 2002) and moreover exhibits homologies with the HARP peptide.

The choice may also be made to use a gene therapy by also expressing a nucleic acid coding for the peptide 150-183 of amphoterin.

The present invention also relates to the use of a nucleic acid comprising a sequence coding for a HARP peptide 13-39 or 65-97, or a peptide derived from one of these, optionally in association with a HARP peptide 111-136 or a derived peptide, for the preparation of a medicament intended to inhibit angiogenesis or intended for the treatment of a pathology associated with an angiogenesis.

The invention further relates to a method of inhibiting angiogenesis or for treating a pathology associated with an angiogenesis in a mammal, more particularly a human, comprising the administration in this mammal of a therapeutically effective quantity of a nucleic acid comprising a sequence coding for a HARP peptide 13-39 or 65-97, or peptide derived from one of these, optionally in association with a nucleic acid comprising a sequence coding for a HARP peptide 111-136 or a peptide derived therefrom.

The following examples and drawings illustrate the invention without limiting the scope thereof.

EXAMPLES

Example 1

Effect of HARP Peptides 13-39 and 65-97 on the Inhibition of the Proliferation of the NIH 3T3 Cells Stimulated by HARP Fibroblast cells of type NIH 3T3 are cultured at a density of $3 \times 10^4$ cells per $cm^2$ in DMEM culture medium supplemented with 10% of foetal calf serum. After 24 hours of incubation at 37° C. in an atmosphere containing 7% of $CO_2$, the culture medium is replaced by DMEM which does not contain foetal calf serum. Twenty-four hours afterwards, the HARP molecule (4 nM) in the presence or absence of the HARP peptides 16-39 or 65-97 of respective sequences SEQ ID NOS: 2 and 3 at a concentration ranging from 0.1 to 10 μM is added over 18 hours. After this period of incubation, 0.5 μCi of [methyl-$^3$H]thymidine is added and 6 hours afterwards the cells are fixed by a 10% solution of trichloroacetic acid. The radioactivity incorporated by the cells is then counted by liquid scintillation after having effected a cell lysis with a solution of sodium hydroxide at a concentration of 0.1 N.

The results are set out in FIG. 1 and show that the peptides corresponding to the sequence 13-39 and 65-97 are capable of inhibiting the activity of induction of the HARP cell proliferation in a dose-dependent manner. At a dose of 10 μM, the peptide 65-97 inhibits more than 90% of the HARP activity, whilst 60% inhibition is observed for the peptide 13-39.

Example 2

Effect of the HARP Peptide 111-136 on the Inhibition of Tumour Angiogenesis and Tumour Growth The capacity of the peptide P111-136 (SEQ ID NO: 4) to inhibit tumour angiogenesis has been tested by inducing tumour growth by injection of PC3 cells into nude mice in the presence or absence of peptide P111-136. $2 \times 10^6$ PC3 cells are injected into groups of 5 nude mice (nude/nude, Laboratoire IFFA CREDO) treated or not by injection in the region of the tumour of 100 μl per day of a solution of PBS (control group) or by a solution of peptide P111-136 diluted in PBS at a concentration of 5 mg/kg. On day 9, 13, 16, 20, 23 and 27 the size of the tumour is measured with the aid of a calliper gauge. The results are presented in FIG. 3 and indicate that the HARP peptide 111-136 used at a dose of 5 mg per kg induces an inhibition of the growth of the tumours.

The analysis of the data indicates that the rate of tumour growth is 4 times less for the mice treated with 5 mg/kg of HARP peptide 111-136 than those which are not treated. On day 27, it is observed that for the group of mice treated, the mean size of the tumours is 80% smaller than in those which have not received treatment.

On day 27, the tumours are removed and freezing sections of 5 μm are produced. After fixing of the tissues with acetone (4° C., 15 min) and rehydration thereof, the presence of the endothelial cells is revealed with the aid of the lectin Bandeiraea Simplicifolia Isolectin B4 (10 μg/ml) which is fixed specifically to the surface of the endothelial cells. This lectin is then detected by immunomarking with the aid of a sandwich of specific antibodies marked with alkaline phosphatase. After incubation with a substrate of alkaline phosphatase (Vector Red substrate), the endothelial cells are stained red. The quantification of the number of endothelial cells in the tumour is carried out by image analysis (NIH image) by analysing the 6 tumours on 3 independent sections of one and the same tumour.

Figure 3:
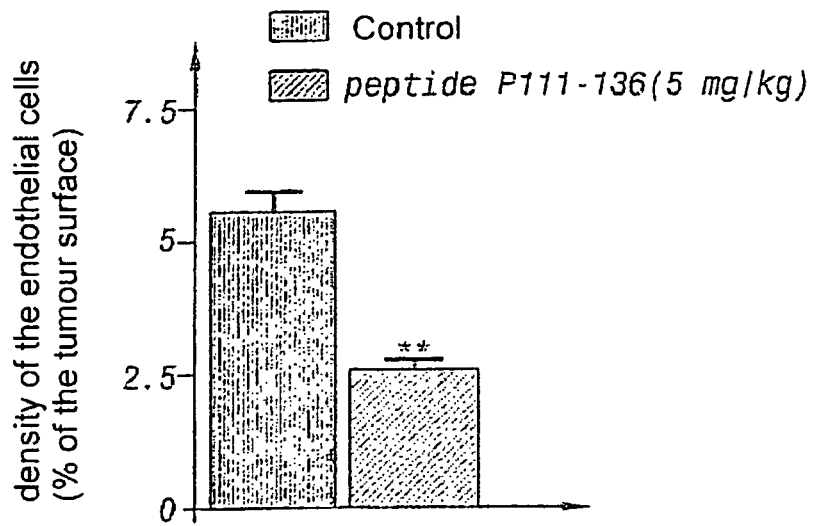
FIG. 3 shows a chart representing the inhibition of tumour angiogenesis in a model of nude mice which have received an injection of PC3 cells (line coming from prostate cancer). Two million PC3 cells are injected into groups of mice treated or not by daily injection in the region of the tumour with PBS (control) or with the peptide 111-136 at a concentration of 5 mg/kg. The mice are sacrificed on day 27. The quantification of the angiogenesis is effected on a section after immunohistological analysis using isolectine *Bandeiraea Simplicifolia* as a specific marker of the endothelial cells and image analysis. The values presented in the histogram represent the mean value obtained by analysing three independent sections resulting from each of six tumours obtained in each condition.

A number of endothelial cells are observed which are less important for the tumours treated by the peptide than for the untreated tumours. The quantification of this effect is shown in FIG. 3. Analysis of the histogram indicates that the injection of the peptide P111-136 induces a 55% reduction in the intra-tumoral vessels, demonstrating that the peptide P111-136 is capable of inhibiting the tumour angiogenesis.

Example 3

Effect of the HARP Peptides 13-39 and 65-97 on the Inhibition of the Growth of Tumour Cells on Soft Agar MDA-MB-231 cells from human mammary carcinoma are cultured at a density of $3 \times 10^3$ cells per $cm^2$ in a DMEM culture medium containing 10% of foetal calf serum, 0.35% of agar and containing or not containing concentrations of HARP peptides 13-39 and 65-97 (SEQ ID NOS: 2 and 3). The cells are cultured in a culture box with 12 wells (35 mm in diameter/well) previously covered with 1 ml of 0.6% agar. The peptides are added into the culture medium every 2 days. After 13 days of incubation in a humid atmosphere at 37° C. and 7% $CO_2$, the colonies having a diameter equal to or greater than 50 μm are counted. Each point in the experiment is carried out in triplicate and each experiment is repeated three times.

Figure 4:
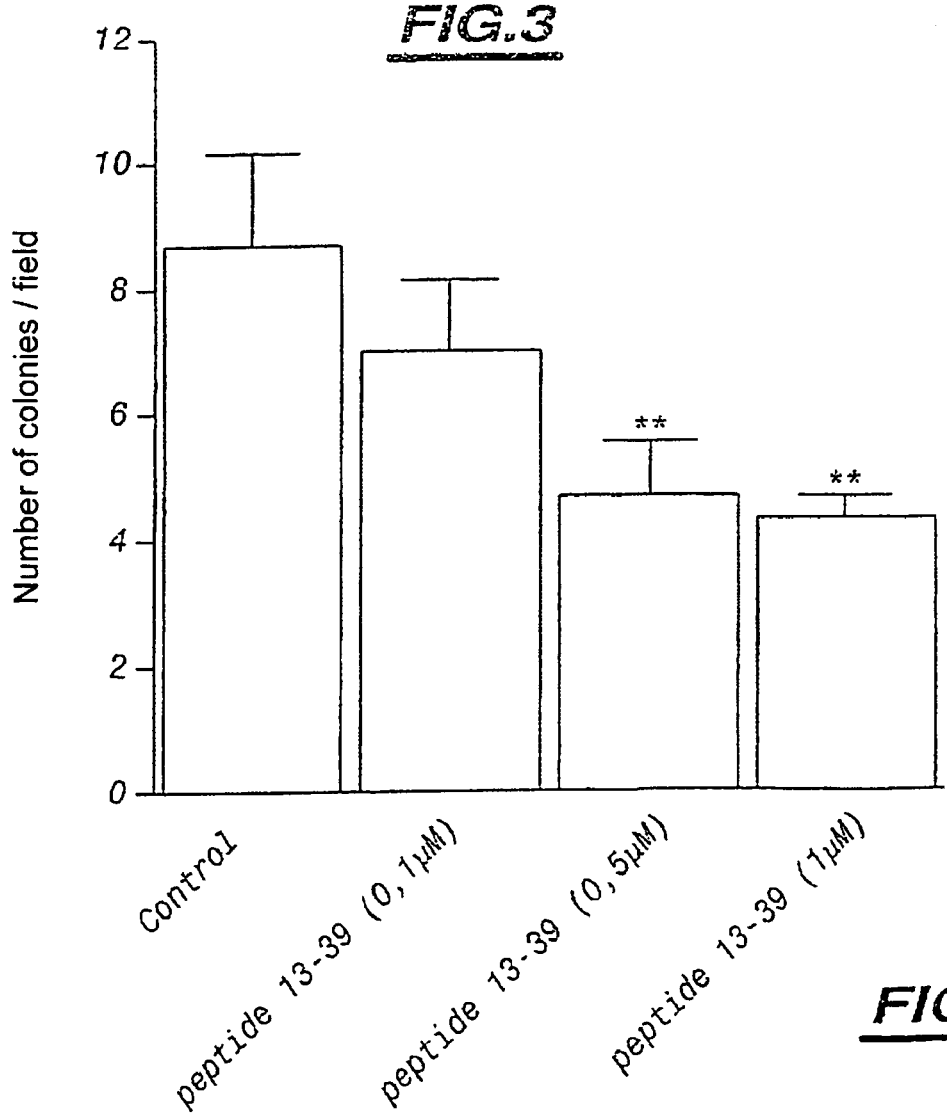
FIG. 4 shows a chart which represents the inhibition of the growth of the tumour cells MDA-MB-231 induced by the HARP peptide 13-39. The MDA-MB-231 cells are cultured in a culture box with 12 wells containing 1 ml of 0.6% agar in the presence or absence of HARP peptide 13-39. After 13 days of culture the colonies having a diameter equal to or greater than 50 µm are counted. The results on the chart represent the values of an experiment repeated 2 times with similar values and each measurement is made in triplicate. The bars represent the standard margins for error (*, $p<0.05$; **, $p<0.01$).
Figure 5:
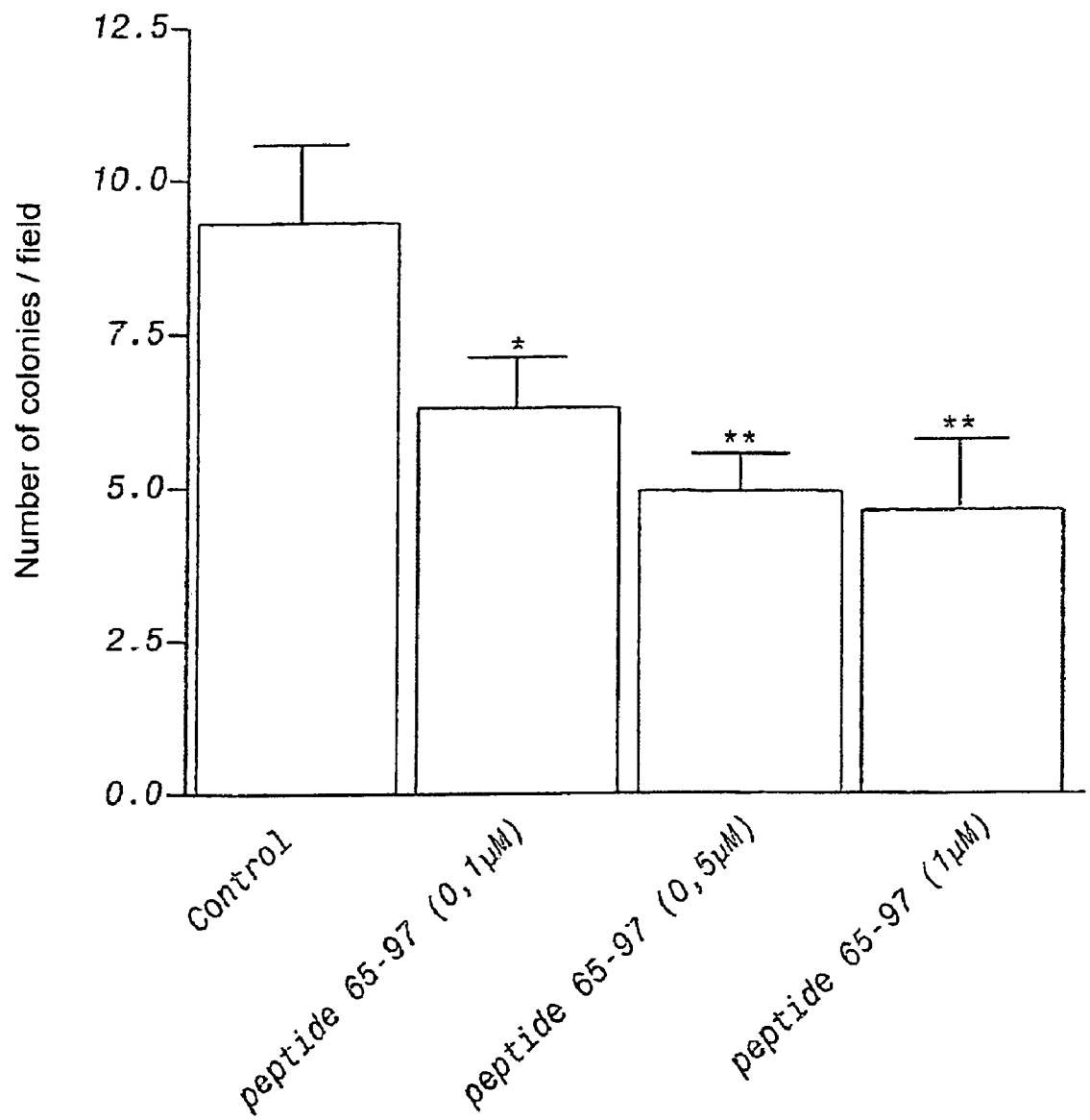
FIG. 5 shows a chart which represents the inhibition of the growth of the tumour cells MDA-MB-231 induced by the HARP peptide 65-97. The MDA-MB-231 cells are cultured in a culture box with 12 wells containing 1 ml of 0.6% agar in the presence or absence of HARP peptide 65-97. After 13 days of culture the colonies having a diameter equal to or greater than 50 µm are counted. The results on the chart represent the values of an experiment repeated 2 times with similar values and each measurement is made in triplicate. The bars represent the standard margins for error (*, $p<0.05$; **, $p<0.01$).

The results represented in FIGS. 4 and 5 show that the HARP peptides 13-39 and 65-97 inhibit the growth of tumour cells in a dose-dependent manner. Thus an inhibition of the growth of the MDA-MB-231 tumour cells of 53% is observed in the presence of 1 μM of HARP peptide 13-39 (FIG. 4) and 41% in the presence of HARP 65-97 used at the same concentration (FIG. 5).

Example 4

Inhibition by the Peptides 13-39 and 65-97 of Angiogenesis Induced by HARP

As HARP is a growth factor implicated in the proliferation and the differentiation of endothelial cells, the inventors have, in the experiment set out below, studied the effect of the HARP peptides 13-39 and 65-97 (SEQ ID NOS: 2 and 3) on the angiogenic activity induced by HARP.

This experiment was carried out using an in vivo angiogenesis model in mice. This experimental model consists in injecting Matrigel® containing a substance to be analysed for its angiogenesis stimulating or inhibiting properties. Four Swiss mice (Janvier, Genest St Isle, France) per group are injected with 300 μl of Matrigel® previously incubated with either 5 nM of HARP, 1 μM of HARP peptide 13-39 or 65-97, or with a mixture of HARP (5 nM) and HARP peptides 13-39 or 65-97 (1 μM). The control of the specificity of the inhibition is carried out using another angiogenic factor, FGF-2, tested either by itself at a concentration of 10 nM or supplemented by the HARP peptides 13-39 or 65-97 used at a concentration of 1 μM.

The mice are sacrificed seven days after the injection of the Matrigel®. This latter is removed and frozen in liquid nitrogen. Sections 8 μM thick are then effected with a cryostat. The sections are then stained with Trichrome from Gomori. The number of endothelial cells which have invaded the Matrigel® is quantified by image analysis using NIH imaging software.

Figure 6:
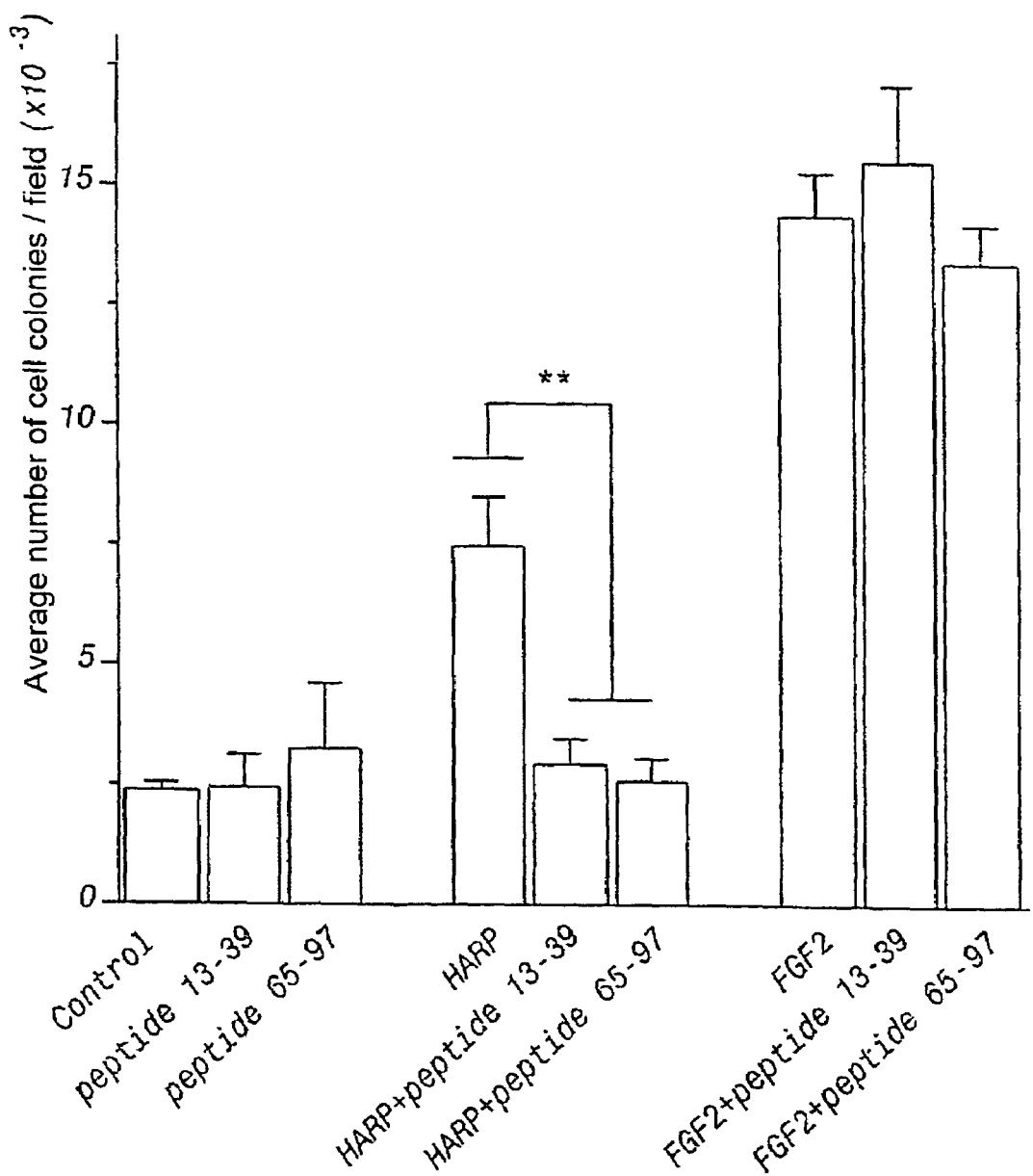

The results set out in FIG. 6 indicate that HARP as well as FGF-2 induce a stimulation of angiogenesis. By comparison with Matrigel® used by itself, an increase in the number of endothelial cells by a factor of 3 is observed for HARP and by 5.8 times for FGF-2. Used at a concentration of 1 μM, the HARP peptides 13-39 or 65-97 totally inhibit angiogenesis induced by HARP whilst they have no effect on angiogenesis induced by FGF-2. No significant effect was observed when the HARP peptides 13-39 or 65-97 are used alone.

These results show that the peptides HARP 13-39 or 65-97 are specific inhibitors of the angiogenic activity induced by HARP.

REFERENCES

Bernard-Pierrot et al (2001) *J Biol Chem* 276, 12228-12234
Bernard-Pierrot et al (2002) *J Biol Chem* 277(35): 32071-7
Chauhan et al (1993) *Proc Natl Acad Sci USA* 90, 679-682
Choudhuri et al (1997) *Cancer Res* 57, 1814-1819
Courty et al (1991) *Biochem Biophys Res Commun* 180, 145-151
Fang et al (1992) *J Biol Chem* 267, 25889-25897
Firat et al, (2002), *J. Gen. Ther.* 4:38-45
Folkman, J. (1971) *N Engl J Med* 285, 1182-1186
Furth et al, (1992) *analytical Biochemistry*, 205:365-368
Jackson et al, (1988) *Ann. Rheum. Dis.* 57(3):158-161)

Jager et al (1997) *Int J Cancer* 73, 537-543
Huttunen et al (2002), *Cancer Research* 62:4805-4811
Kojima et al (1995a) *Biochem Biophys Res Commun* 216, 574-581
Kojima et al (1995b) *Biochem Biophys Res Commun* 206, 468-473
Ledoux et al (1997) *J Histochem Cytochem* 45, 1239-1245
Matsubara et al (1990) *J Biol Chem* 265, 9441-9443
Milhiet et al (1998) *J Endocrinol* 158, 389-399
Novotny et al (1993) *Arterioscler Thromb* 13, 1798-1805
Papadimitriou et al (2000) *Biochem Biophys Res Commun* 274, 242-248
Papadimitriou et al (2001) *Biochem Biophys Res Commun* 282, 306-313
Rauvala, H. (1989) *Embo J* 8, 2933-2941
Riegel et al (1994) *Breast Cancer Res Treat* 31, 309-314
Robinson et al, (1997) *Immunology* 9: 271-83
Sambrook (1989) Cold Spring Harbor Laboratory Press, Cold Spring Harbor, New York
Stoica et al (2001) *J Biol Chem* 276, 16772-16779
Taguchi et al (2000) *Nature* 405: 354-360
Tang et al, (1992) *Nature* 356, 152-154
Tsutsui et al (1991) *Biochem Biophys Res Commun* 176, 792-797
Vacherot et al (1999a) *Prostate* 38, 126-136
Vacherot et al (1999b) *J Biol Chem* 274, 7741-7747
Wellstein et al (1992) *J Biol Chem* 267, 2582-2587
Yeh et al (1998) *J Neurosci* 18, 3699-3707

---

The invention claimed is:

1. An isolated peptide consisting of the amino acid sequence SEQ ID NO: 2 or SEQ ID NO: 3.

2. A pharmaceutical composition comprising an isolated peptide consisting of the amino acid sequence SEQ ID NO: 2 or SEQ ID NO: 3, and at least one pharmaceutically acceptable excipient.

3. The pharmaceutical composition of claim 2, further comprising a peptide consisting of the amino acid sequence of SEQ ID NO: 4.

4. The pharmaceutical composition of claim 3, comprising:
(a) the peptide consisting of the amino acid sequence of SEQ ID NO: 2;
(b) the peptide consisting of the amino acid sequence of SEQ ID NO: 3; and
(c) the peptide consisting of the amino acid sequence of SEQ ID NO: 4.

5. A method for preparing a medicament for the treatment of tumors, comprising adding an isolated peptide consisting of the amino acid sequence SEQ ID NO: 2 or SEQ ID NO: 3 to a pharmaceutically acceptable vehicle.

6. The method of claim 5, wherein said isolated peptide is combined with a second peptide consisting of the amino acid sequence of SEQ ID NO: 4.

* * * * *